United States Patent
Blanchard et al.

(10) Patent No.: US 9,080,979 B2
(45) Date of Patent: Jul. 14, 2015

(54) SINGLE MOLECULE IMAGING TECHNIQUES TO AID CRYSTALLIZATION

(75) Inventors: Scott C. Blanchard, New York, NY (US); Michael Brian Feldman, Setauket, NY (US); Leyi Wang, New York, NY (US); Roger Altman, New York, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 14/111,950

(22) PCT Filed: Apr. 14, 2012

(86) PCT No.: PCT/US2012/033698
§ 371 (c)(1),
(2), (4) Date: Oct. 15, 2013

(87) PCT Pub. No.: WO2012/142541
PCT Pub. Date: Oct. 18, 2012

(65) Prior Publication Data
US 2014/0093870 A1    Apr. 3, 2014

Related U.S. Application Data

(60) Provisional application No. 61/476,102, filed on Apr. 15, 2011.

(51) Int. Cl.
*G01N 21/64* (2006.01)
*G01N 33/542* (2006.01)
*C30B 29/58* (2006.01)

(52) U.S. Cl.
CPC .......... *G01N 21/6486* (2013.01); *G01N 33/542* (2013.01); *C30B 29/58* (2013.01)

(58) Field of Classification Search
None
See application file for complete search history.

(56) References Cited

U.S. PATENT DOCUMENTS

2007/0105196 A1    5/2007    Lukyanov

FOREIGN PATENT DOCUMENTS

| EP | 1172646 A1 | 1/2002 |
| EP | 2194376 A2 | 6/2010 |
| RU | 2412250 C2 | 12/2009 |
| WO | WO 2010/096720 | 8/2010 |

OTHER PUBLICATIONS

Blanchard, S.C. et al., tRNA dynamics on the ribosome during translation, PNAS, (Aug. 31, 2004), vol. 101, No. 35, pp. 12893-12898.
Brandt, F. et al., The Native 3D Organization of Bacterial Polysomes, Cell, (Jan. 23, 2009), vol. 136, pp. 261-271.
Munro, J.B. et al., A fast dynamic mode of the EF-G-bound ribosome, The EMBO Journal, (2010), vol. 29, No. 4, pp. 770-781.
Munro, J.B. et al., Spontaneous formation of the unlocked state of the ribosome is a multistep process, PNAS, (Jan. 12, 2010), vol. 107, No. 2, pp. 709-714.
Zhang, W. et al., Structures of the Ribosome in Intermediate States of Ratcheting, Science, (Aug. 31, 2009), vol. 325, pp. 1014-1017.
Munro, J.B. et al., Navigating the ribosome's metastable energy landscape, Trends in Biochemical Sciences, (Aug. 2009), vol. 34, No. 8, pp. 390-400.
Schmeing, T.M. et al., What recent ribosome structures have revealed about the mechanism of translation, nature, (Oct. 29, 2009), vol. 461, pp. 1234-1242.
Akyuz, N., et al., Transport domain unlocking set that uptake rate of an aspartate transporter, Nature, (Feb. 5, 2015), vol. 518, pp. 68-86.
Pancera, M. et al., Structure and immune recognition of trimeric pre-fusion HIV-1 Env, Nature, (Oct. 23, 2014), vol. 514, pp. 455-488.

*Primary Examiner* — Nashaat Nashed
(74) *Attorney, Agent, or Firm* — Scully, Scott, Murphy & Presser, P.C.

(57) ABSTRACT

This invention relates to a method to rapidly find crystallization conditions for a biomolecule in a desired conformation using single-molecule, fluorescent resonance energy transfer (smFRET) imaging techniques. The method provides significant cost and time advantages over the empricial exploration for crystallization conditions.

15 Claims, 4 Drawing Sheets

SINGLE MOLECULE IMAGING TECHNIQUES TO AID CRYSTALLIZATION

CROSS-REFERENCE TO RELATED APPLICATIONS

This application claims priority from U.S. Provisional Application No. 61/476,102, filed Apr. 15, 2011, which is herein incorporated by reference in its entirety.

GOVERNMENT FUNDING

This invention was made with Government support under Grant Numbers GM65050 and GM079238 awarded by the National Institutes of Health. The United States Government has certain rights in the invention.

FIELD OF THE INVENTION

This invention relates to a method to rapidly find crystallization conditions for a biomolecule in a desired conformation using single-molecule, fluorescent resonance energy transfer (smFRET) imaging techniques. The method provides significant cost and time advantages over the empirical exploration for crystallization conditions.

INCORPORATION BY REFERENCE OF SEQUENCE LISTING

The Sequence Listing in an ASCII text file, named 27554_5467_04_SequenceListing.txt of 1 KB, created on Nov. 13, 2013, and submitted to the United States Patent and Trademark Office via EFS-Web, is incorporated herein by reference.

BACKGROUND OF THE INVENTION

Protein biosynthesis by the ribosome proceeds in defined phases of initiation, protein elongation, termination, and ribosome recycling (Schmeing 2009). Understanding the molecular mechanism of translation requires high-resolution descriptions of the motions in the ribosome that enable key translational events (Munro 2009; Schmeing 2009; Dunkle 2010). A ratchet-like rotation of the small ribosomal subunit relative to the large ribosomal subunit (Frank 2000) is crucial to the positioning of tRNAs in intermediate—or hybrid—binding sites, in which the 3'-CCA termini and acceptor stems of tRNA advance by one site on the large subunit while the anticodon elements of tRNA remain fixed on the small subunit (Moazed 1989). Binding of tRNAs in hybrid sites is central to mRNA and tRNA movements on the ribosome when they are translocated after peptide bond formation, during termination, and during ribosome recycling (Semenkov 2000; Zavialov 2003). However, the molecular basis for ribosome positioning of tRNAs in hybrid sites has been unclear.

Atomic resolution x-ray crystal structures of the bacterial ribosome with ligands bound have revealed molecular details of conformational rearrangements taking place in the unratcheted ribosome (Schmeing 2009). The first molecular descriptions of intermediate states of ribosome ratchet-like rotation at atomic resolution were provided by x-ray crystal structures of the E. coli 70S ribosome (Zhang 2009), with additional sub-steps proposed based on cryo-EM reconstructions (Fischer 2010). A post-translocation rotated state of the ribosome was recently identified by cryo-EM (Ratje 2010), in a conformation similar to that of the Saccharomyces cerevisiae 80S ribosome in the absence of bound substrates (Ben-Shem 2010).

Figure 1:
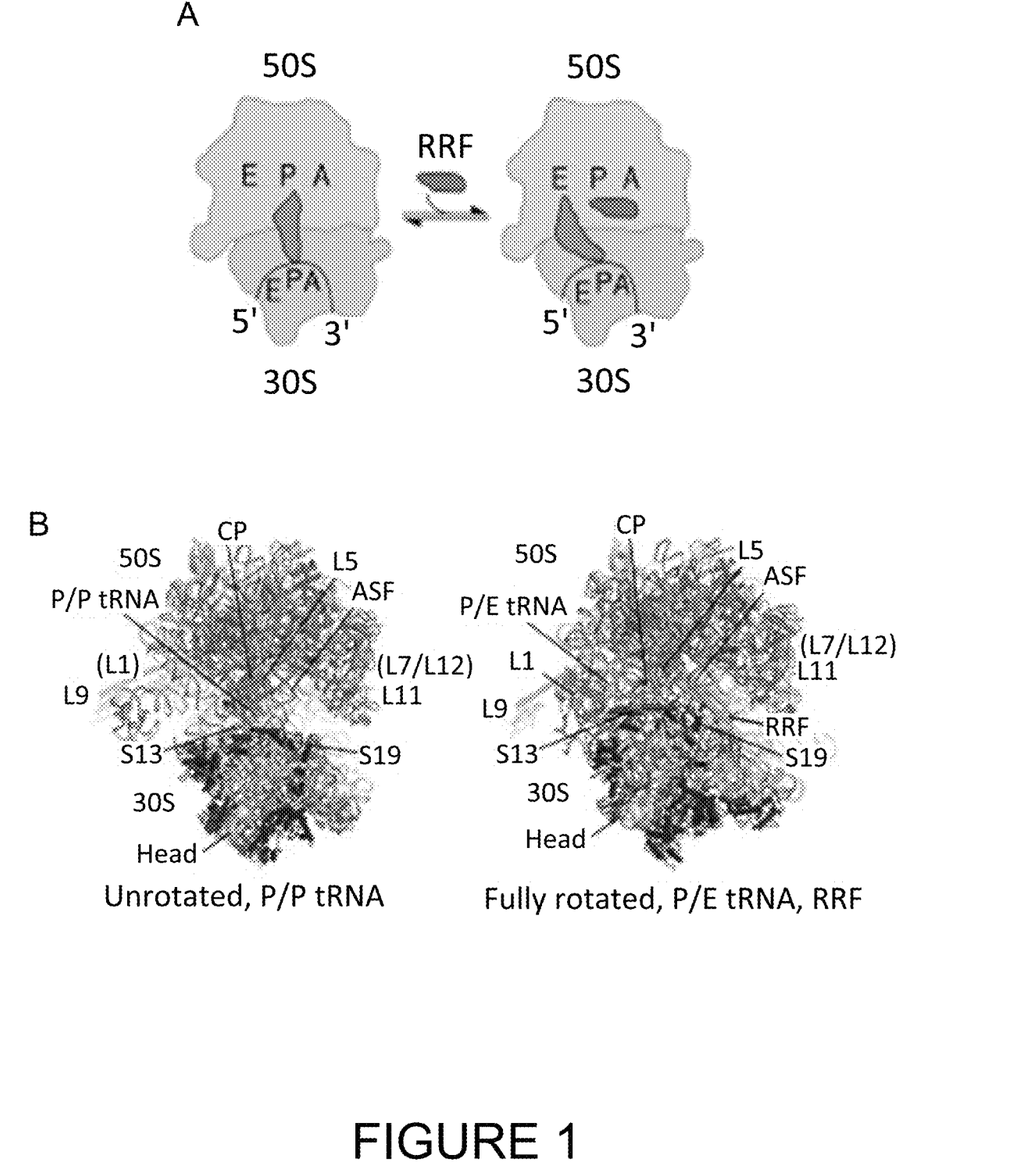

After the termination of protein synthesis, ribosome recycling is required to free ribosomes from the mRNA transcript to enable further rounds of translation. In bacteria and organelles, ribosome recycling factor (RRF) binds in the tRNA binding cleft of the 70S ribosome at the interface of the large (50S) and small (30S) subunits and interacts with the 50S subunit peptidyl transferase center (PTC) (Lancaster 2002; Agrawal 2004). In so doing, RRF sterically occludes deacylated tRNA binding in the peptidyl-tRNA site (P site, P/P configuration) to favor tRNA positioning in the hybrid peptidyl/exit tRNA binding site (P/E configuration) (FIG. 1A) (Gao 2005; Sternberg 2009). In the P/E configuration, tRNA is bound simultaneously to the P site of the small (30S) subunit and to the E site of the large (50S) subunit (Moazed 1989). Binding of the GTPase elongation factor-G (EF-G) to the RRF-ribosome complex and subsequent GTP hydrolysis lead to the dissociation of ribosomal subunits (Savelsbergh 2009).

Crystallization of biomolecules generally proceeds by empirical exploration of potential crystallization conditions and is a slow and arduous process, even when considerable structural information may already be available. For example, if the biomolecule of interest is known to exist in, or to sample, multiple conformational states, as is the case with the ribosome during the defined phases of initiation, protein elongation, termination, and ribosome recycling, and one of those states is thermodynamically favored, it may be very difficult to find suitable crystallization conditions from which to crystallize the biomolecule into a different conformational state. Hence, providing a method to rapidly vary solution conditions while simultaneously sampling the conformational states of the biomolecule across those conditions, would allow one to rapidly ascertain the parameters important for maintaining the alternate conformational state. Such an ability would be invaluable for optimizing crystallization conditions to favor a desired conformation of a biomolecule because one can alter the energy landscape so that the "normally transient" conformation becomes favored under the solution conditions identified through screening. As shown herein, single-molecule, fluorescence resonance energy transfer (smFRET) imaging methods are adaptable to rapid screening techniques and can provide the type of information needed to optimize crystallization conditions to stabilize a specific conformation of a biomolecule.

For example, prior to the present work, high-resolution (e.g., atomic resolution) structures of all functionally relevant ribosome complexes were found to occupy the classical, unrotated conformation. The use of smFRET imaging methods showed the likely reason for this empirical observation is that the bacterial ribosome is thermodynamically more stable in this configuration. Thus, to determine the structure of the hybrid, rotated ribosome conformation, smFRET imaging methods were used to establish experimental conditions in which functional ribosome complexes were "stabilized" in the desired conformation (e.g., hybrid tRNA, "unlocked state" configuration). These conditions, which were rapidly determined by smFRET imaging, and enabled crystallization of the ribosome in this rotated configuration.

Hence, single-molecule imaging techniques can be used to rapidly optimize solution conditions, screen including the presence or absence of one or more ligands, if applicable, or even screen mutants, to generate crystals of a biomolecule in a desired conformation.

SUMMARY OF THE INVENTION

The present invention relates to methods of using single-molecule imaging techniques to optimize buffer and co-crystallized ligand conditions in order to generate crystals of biomolecules in a desired conformation.

In particular, the methods are directed to determining optimal crystallization conditions for a biomolecule in a desired, or specific, conformation by (a) identifying one or more desired conformations of the biomolecule; (b) preparing a biomolecule with a donor fluorophore and an acceptor fluorophore sufficiently spaced to detect FRET signal changes when said biomolecule transitions between specific conformations or to detect FRET changes in distribution of or time spent by the biomolecule in specific conformations; (c) imaging the biomolecule using smFRET under varying conditions while detecting the FRET changes; and (d) selecting as the crystallization conditions, those conditions in which the biomolecule increases its distribution of or time in a desired conformation or is stabilized in a desired conformation. In some instances, the desired conformation can be representative of (or report on) multiple conformations.

In accordance with the method, varying the conditions under which the smFRET data is collected can be accomplished by varying buffers, pH, temperature, salts and/or adding salting in or salting out agents, one or more ligands for the biomolecule, conducting the method using mutants of the biomolecule.

The method of the invention is applicable to many types of biomolecules, including those made of single molecules or complexes multiple subunits. In this regard the fluorophore pairs can be on the same subunit or differing subunits of the said biomolecule, provided they are sufficiently space to detect FRET changes when the biomolecule transitions between or among conformational states.

In some embodiments, the biomolecules used in the methods of the invention include proteins, peptides, proteoliposomes, nucleic acids, oligonucleotides, and/or complexes of any of the foregoing. The individual components can optionally have a small molecule associated with them; similarly, the complexes can optionally comprise a small molecule. Examples of biomolecules include but are not limited to, RNA protein complexes such as a ribosome, a splicesome, a telomerase or a microRNA complex; RNA such as a riboswitch or a ribozyme; membrane proteins such as aviral envelope protein, an ion channel, an EAAT transporter protein, an MFS transporter protein, an ABC transporter or a P-type ATPase; as well as other biomolecules such as GPCR, an NSS protein, a protein kinase, an aminoacyl-tRNA synthetase, a caspase or a motility or motor protein such as kinesin or myosin.

The method can be adapted for high throughput screening and analysis of potential crystallization conditions.

BRIEF DESCRIPTION OF THE DRAWINGS

FIG. 1 illustrates ribosome recycling in bacteria and organelles. Panel A is a schematic drawing showing the steps of ribosome recycling. After termination, ribosomes with deacylated tRNA in the P site undergo a structural rearrangement to a fully rotated state in which tRNA adopts a P/E hybrid state of binding and RRF is bound in the 50S P site. EF-G then catalyzes subunit dissociation. Panel B shows global views of the ribosome in an unrotated, post-termination state (left) and in a fully rotated, intermediate state of recycling (right). The small subunit rRNA and proteins at the bottom of the complex are colored lighter and darker, respectively, with the large subunit rRNA and proteins at the top of the complex colored lighter and darker, respectively. Bound tRNA (dark form in center of image A), mRNA and RRF are also shown.

FIG. 2 illustrates the dependence of subunit release on RRF, EF-G and GTP under crystallographic buffer conditions. Release was monitored by the loss of Cy5-labeled L1 fluorescence in 50S subunits from surface-immobilized ribosome complexes carrying Cy3-labeled tRNA$^{Phe}$ in the P site. Complexes imaged in the absence of factors (diamonds) or in the presence of 10 µM RRF (circles); 20 µM EF-G and 2 mM GTP (inverted triangles); 10 µM RRF, 20 µM EF-G and 2 mM GDPNP (triangles); or 10 µM RRF, 20 µM EF-G and 2 mM GTP (squares). Data reflect the mean±SD of normalized Cy5 fluorescence intensity as a function of time from three experimental replicates.

FIG. 3 illustrates the dynamic interactions between the L1 stalk and P-site tRNA$^{Phe}$. As previously reported (Munro 2010), complexes bearing (Cy5-S55C) L1 protein and (Cy3-s$^4$U8) tRNA$^{Phe}$ achieve a high-FRET state upon the simultaneous occurrence of hybrid state formation (P/E) and L1 stalk closure. FIG. 3A depicts representative single-molecule fluorescence and FRET trajectories obtained from a ribosome complex bearing Cy3 labeled deacylated P-site tRNA$^{Phe}$ and Cy5 labeled L1 protein, imaged at 40 millisecond time resolution in buffer conditions similar to those used in crystallographic experiments. Idealization of the smFRET trajectory, as previously described (Munro 2010), is overlaid. The boxed region in the upper panel shows an expanded region of the smFRET trajectory. FIG. 3B shows the individual FRET trajectories summed into population FRET histograms to reveal changes in the relative distribution of FRET states occupied with increasing RRF concentrations. FIG. 3C graphically illustrates RRF-induced stabilization of the unlocked state of the ribosome (hybrid P/E tRNA; closed L1 stalk), detected by the decrease in transition rate out of a high-FRET state between Cy5-labeled protein L1 and Cy3-labeled P-site tRNA$^{Phe}$. The apparent $K_d$ for RRF based on the decrease in the transition rate is 5.7 µM.

DETAILED DESCRIPTION OF THE INVENTION

In the following description, reference is made to the accompanying drawings that form a part hereof, and in which is shown by way of illustration specific embodiments which may be practiced. These embodiments are described in detail to enable those skilled in the art to practice the invention, and it is to be understood that other embodiments may be utilized and that logical changes may be made without departing from the scope of the present invention. The following description of example embodiments is, therefore, not to be taken in a limited sense, and the scope of the present invention is defined by the appended claims.

Definitions

"Single-molecule fluorescence resonance energy transfer" (or "smFRET") is the application of FRET techniques to study a single molecule with at least two fluorescent labels, or the interaction of at least two molecules, each with a label. Fluorescence Resonance Energy Transfer (FRET) is a non-radiative pathway by which a molecule in an electronic excited state may relax back to the more stable ground state. The transfer of energy occurs through space via dipole-dipole interaction: energy from the excited state molecule (the donor fluorophore) may transfer to a neighboring molecule (the acceptor fluorophore) given significant degree of spectral overlap between donor emission and acceptor absorption, properly oriented dipole moments of the interacting dye molecules, and the appropriate distance between the two flourophores. The Forster relationship defining the efficiency of FRET as a function of distance is unique for each dye pair. In smFRET the donor and receptor fluorophores are on the same molecule, or are on different molecules that interact, bringing the two fluorophores into proximity. The detection of FRET at the single-molecule scale enables the direct measurement of conformational events and/or binding processes on biologically-relevant time scales. Methods to perform smFRET imaging are known in the art, and are described, for example, in Blanchard 2004.

Dynamic smFRET refers to the use of smFRET techniques to interrogate biological samples of interest over extended periods of time in order to quantify changes in the amount of time that the sample spends in its various conformational states. By measuring time-dependent conformational dynamics in a biomolecule, insights into the physical parameters of motion are obtained that relate to regulation and function.

The labels used herein will generally comprise fluorophores, and can use donor-acceptor pairs or donor-quencher pairs. A "fluorophore" is a component of a molecule which causes a molecule to be fluorescent. It is a functional group in a molecule which will absorb energy of a specific wavelength and re-emit energy at a specific wavelength. The amount and wavelength of the emitted energy depend on both the fluorophore and the chemical environment of the fluorophore. Fluorescein isothiocyanate (FITC), a reactive derivative of fluorescein, has been one of the most common fluorophores chemically attached to other, non-fluorescent molecules to create new fluorescent molecules for a variety of applications. Other common fluorophores are derivatives of rhodamine (TRITC), coumarin, and cyanine. Newer generations of fluorophores such as the fluorescent dyes sold under the trade name CF™ dyes, Cyanin (Cy) dyes, the fluorescent dyes sold under the trade name FLUOPROBES®, the fluorescent dyes sold under the trade name DYLIGHT FLUORS, the fluorescent dyes sold under the trade name OYSTER®, the fluorescent dyes sold under the trade name ATTO, the fluorescent dyes sold under the trade name HILYTE™, and the fluorescent dyes sold under the trade name ALEXAFLUOR are claimed to be perform better (more photostable, brighter, and/or less pH-sensitive) than other standard dyes of comparable excitation and emission. Fluorophores especially useful for practicing the instant invention are described in PCT application PCT/US10/24824 which is incorporated herein in its entirety by reference.

The fluorophore may incorporate or be located proximally to a "protective agent" (or "quencher" or "triplet state quencher" or "fluorescence modifier", in particular embodiments), which is a molecule or a moiety (i.e., chemical group) that has the ability to alter the photophysical properties of a fluorophore, particularly by altering the light state-dark state (i.e., singlet-triplet) occupancy distribution or relaxation pathway of excited and relaxing electrons. The ability of a molecule to function as a protective agent is often evidenced by its ability to alter the blinking and/or photobleaching characteristics of a fluorophore.

Those of skill in the art can readily select appropriate donor-acceptor pairs for FRET in accordance with the invention as well as modify the biomolecules of the invention to attach the donor and acceptor fluorophores in site-specific manner without substantially altering functionality of the biomolecule.

Description

The present invention is directed to a method to rapidly determine optimal crystallization conditions for a biomolecule in a desired conformation using single-molecule imaging techniques to identify conditions that stabilize the biomolecule in the desired conformation. Generally, this technique is applicable to biomolecules for which some structural information is available, and particularly for biomolecules that exist in multiple conformations (such as might be known, e.g., via NMR, EM imaging, or a spectral technique).

Once a desired conformation of the biomolecule has been recognized or identified, the biomolecule can be labeled with donor and acceptor fluorophores that are spaced at a sufficient distance to exhibit FRET signal changes when the biomolecule transitions between the desired conformation and one or more other conformations. The biomolecule is then imaged using smFRET under varying conditions to detect the FRET changes.

The types of conditions that can be varied are manifold and include but are not limited to, buffers, pH, temperature, salts (ions), chelators, precipitants, the ligands of the biomolecule (including wild type ligands and mutant ligands), number of ligands (e.g., in multisubunit complexes), any molecule which binds to the biomolecule and mutant forms of the biomolecule. Further for those biomolecules that bind or interact with small molecules, the concentrations of those molecules can be varied or one can use homologs or analogs thereof as an alternative. Examples of such small molecules are vitamins, metals, nucleotides and the like.

Examples of useful buffers include, but are not limited to, various Tris acetate and other Tris buffers; TAPS (3-{[tris (hydroxymethyl)methyl]amino}propanesulfonic acid); Bicine (N,N-bis(2-hydroxyethyl)glycine); Tris(tris(hydroxymethyl)methylamine); Tricine (N-tris(hydroxymethyl) methylglycine); TAPSO (Tris(hydroxymethyl)methylamino]-2-hydroxypropanesulfonic Acid); HEPES (4-2-hydroxyethyl-1-piperazineethanesulfonic acid); TES (2-{[tris(hydroxymethyl)methyl]amino}ethanesulfonic acid); MOPS (3-(N-morpholino)propanesulfonic acid); PIPES (piperazine-N,N'-bis(2-ethanesulfonic acid); Cacodylate (dimethylarsinic acid); SSC (saline sodium citrate); MES (2-(N-morpholino)ethanesulfonic acid) and the like.

Temperature ranges that can be selected, range from the tolerance limit of the smFRET equipment through the range of temperatures that the transitions can be observed at without functionally affecting the biomolecule. Moreover, the temperature variation can be done stepwise. For example, temperatures can be changed one half of one degree, so that each temperature condition differs from the next by one half of one degree; or by 1 degree, by 2 degrees, by 3 degrees, by 4 degrees, by 5 degrees or by be ten degrees, or even larger ranges consistent with the properties of the biomolecule. The dynamics of the transitions can influence the temperature interval selected for variation.

Chelating agents include, but are not limited to, EDTA, phosphonates, amino acids (i.e. glycine, histidine), organic diacids (i.e. malate), polypeptides (i.e. phytochelatin) and the like. Salts include, but are not limited to, potassium chloride, sodium chloride, ammonium Chloride, ammonium sulfate, sodium acetate and other salts that are compatible with the biomolecule of interest. Salting out agents include PEGs, ammonium sulfate and the like.

Generally most biomolecules are maintained or active at physiological pH. However if a desired conformation is pH dependent, that can provide a starting point. Hence, from any given pH, and then varying up or down, pH variations can be done incrementally, for example by 0.1, 0.25, 0.5 or 1 pH unit.

Typically, the biomolecules are in contact with various solutions of the different compositions to be interrogated during the smFRET imaging. Temperature and pH can be varied in situ. All such variations are contemplated as part of the "solution conditions" used to interrogate the biomolecule. Moreover, all the operations to vary conditions can be automated using robots to prepare and dispense solutions, alter temperature or pH, to add components and the like using multi-well or configured systems compatible with smFRET imaging conditions.

Once the data is acquired and analyzed, those solution conditions which stabilize the biomolecule in a desired conformation are selected as crystallization conditions. Optimal crystallization conditions are those which maintain the biomolecule in the desired conformation at least the majority of the time or which have at least a majority of the biomolecule in the desired conformation.

The use of single-molecule fluorescence and FRET techniques described and exemplified through the present investigation can be generalized for all biomolecules, which include, but are not limited to, biological polymers (e.g. proteins and nucleic acids) and polymer assemblies (e.g., the ribosome, RNA polymerase, proteosome, chromatin etc) that have evolved to be conformationally dynamic, where the dynamic properties of the system (e.g., the transit between two or more globally distinct conformations) is directly linked to functional activities that can be targeted for therapeutic purpose. For instance, integral membrane proteins responsible for the transport of amino acids across the lipid bilayer must undergo conformational transitions that enable the protein to bind substrate on the extracellular surface of the cell, and release the substrate into the intracellular milieu without forming a channel; G-protein coupled receptors promote signal transduction cascades by undergoing conformational changes and/or multimerization events that signal to the interior of the cell as a consequence of extracellular ligand binding; kinases undergo conformational transitions between "inhibited" and "activated" forms in response to specific queues in a regulated fashion. In each case, the process of structure determination is largely driven by a "trial and error" approach and massively parallelized crystallographic screening methods, where prior to the point of structure determination very little is typically known about the thermodynamically favored conformation of the molecule or whether it is preferentially stabilized in the desired or even new conformation. By employing smFRET imaging, one can dramatically improve the crystallographic hit and success rate by pre-screening crystallographic conditions using any number of site-specifically labeled biomolecules of interest to explore and understand the nature of the system's intrinsic dynamics and its responsiveness to ligand interactions. This approach is advantageous and more cost effective that existing technological and/or methodological approaches as single-molecule methods require only minute amounts of material and data collection/processing can be automated so that results of screening experiments can be returned in nearly real time.

Hence, in the case of the ribosome, iteratively screening buffer conditions (e.g., buffer pH, ionic strength, magnesium ion concentration, buffer composition, temperature) in the presence and absence of translation factors that bind the ribosome (e.g., RRF) has the net effect of altering the kinetic and/or thermodynamic properties of the system. To find potential crystallization conditions, the solutions conditions were those that stabilized the configuration of the ribosome in which high-FRET was observed between fluorescent dyes linked site-specifically to P-site tRNA and the large subunit ribosomal protein L1, which had previously been shown to occur when P-site tRNA adopts a hybrid configuration, the L1 stalk closes and the small subunit adopts a rotated configuration. Initial hits were then subjected to crystallization trials, where a strong correlation between smFRET imaging conditions and crystallographic performance and structural configuration of the system was observed allowing navigation of the otherwise obscure N-dimensional landscape of conditions to achieve the desired ribosome conformation in an experimentally directed fashion.

Figure 2:
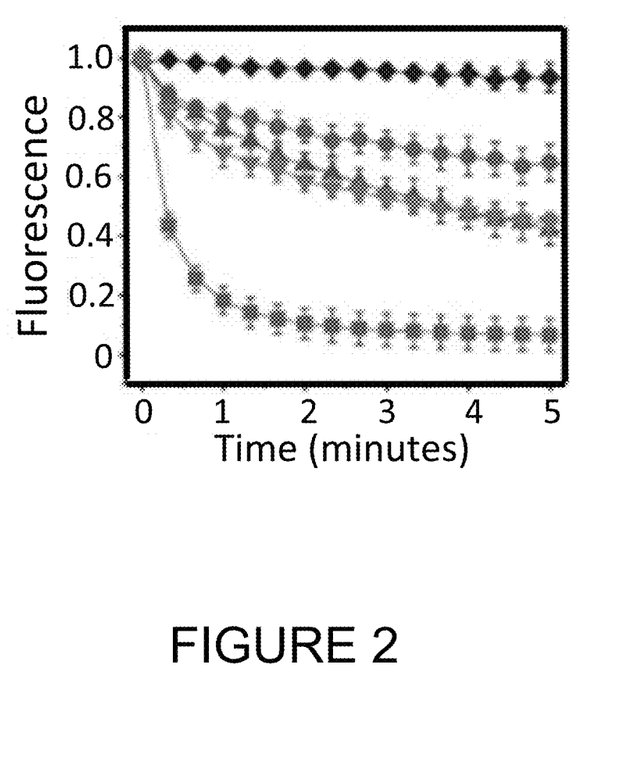
Figure 3:
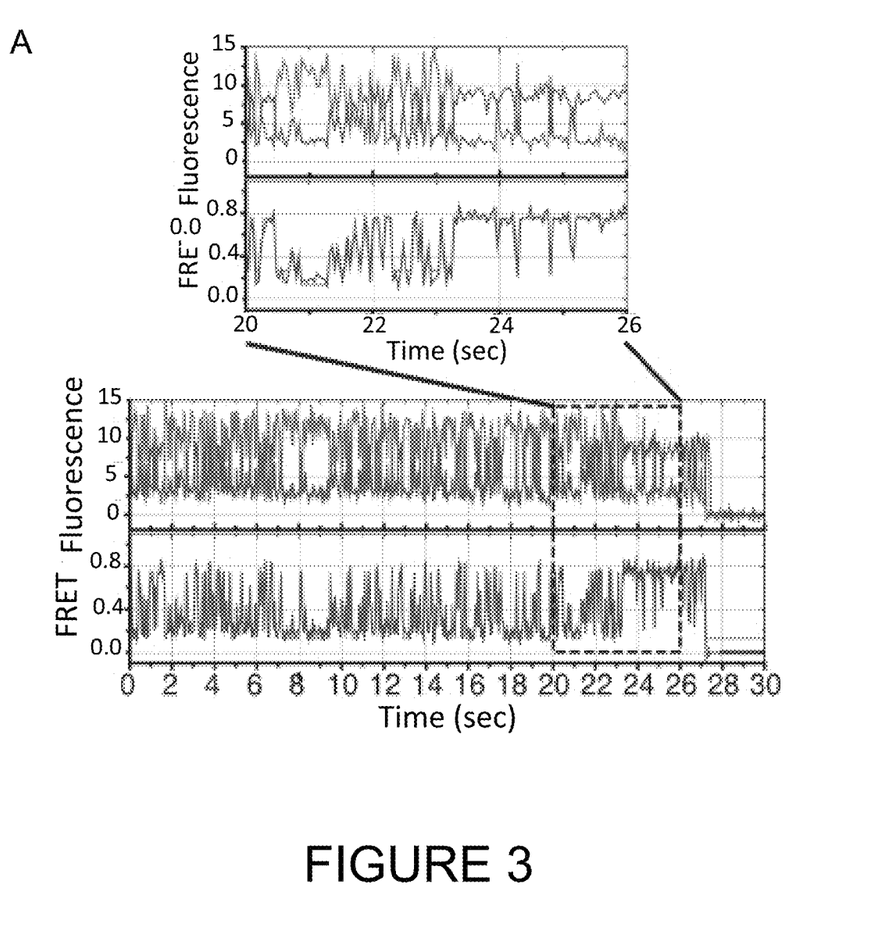

Under these buffer conditions, smFRET measurements showed RRF achieved approximately 50% maximal stabilization of the fully rotated, P/E hybrid configuration of the post-termination complex (FIG. 3) and supported EF-G- and GTP hydrolysis-dependent ribosome recycling (FIG. 2, FIG. 3).

Modifications to any biomolecule used herein may include mutations to improve desired functions of the ribosome or to increase or decrease the likelihood that the biomolecule will take a certain conformation or movement. Modifications may also include means to anchor the biomolecule to a substrate for imaging purposes. For example, a biotin moiety may be added at a location on the biomolecule that does not interfere with function or with the desired conformational state. For the ribosome, tethering functions have been added at the 5' end of the ribosome itself or to an mRNA that forms part of the complex using methods known in the art.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention. All references patents, patent applications, PDB data or other documents cited are herein incorporated by reference in their entirety.

EXAMPLES

Purification of Native E. Coli tRNA$^{Phe}$

The purification protocol for tRNA$^{Phe}$ was adapted from a published protocol (Cayama 2000). Briefly, Escherichia coli (E. coli) cells (strain MRE600) harboring plasmid pBS-tRNA$^{Phe}$, which overexpresses E. coli tRNA$^{Phe}$, were cultured and harvested as previously described (Junemann 1996). The cell pellets were lysed by sonication in 20 mM Tris HCl, pH 7.5, 50 mM MgCl$_2$ and 20 mM β-mercaptoethanol. The cell lysate was clarified by centrifugation at 35000 rpm in a Beckman Ti-70 rotor at 4° C. for 2 hours. Total cellular RNA was extracted from the supernatant by phenol extraction and ethanol precipitation. High molecular weight RNAs were removed by isopropanol precipitation (von Ehrenstein 1967). The soluble RNA fraction was then incubated for 15 min at 37° C. after adjusting the pH to 8 by addition of 0.5 M Tris HCl, pH 8.8 to deacylate tRNAs. As previously described (Blanchard 2004), tRNA$^{Phe}$ was specifically aminoacylated following brief incubation with phenylalanine, ATP and phenylalanyl-tRNA synthase. The reaction mixture was phenol extracted and the nucleic acid fraction was obtained by ethanol precipitation. After resuspending the pellet in 10 mM ammonium acetate pH 6.3, the sample was applied to a TSK Phenyl 5PW hydrophobic interaction column (Tosoh Bioscience) and Phe-tRNA$^{Phe}$ was purified by fractionation as previously described (Blanchard 2004). The isolated peak was desalted, deacylated by brief incubation at elevated pH and repurified using analogous methods.

Ribosome Recycling Factor Purification.

RRF was purified from E. coli strain BL21 Star cells (Invitrogen) expressing a C-terminal hexa-histidine tagged version of the protein. Cells were lysed by sonication in lysis buffer (50 mM HEPES, pH 7.6, 1 M NH$_4$Cl, 10 mM MgCl$_2$, 200 µM PMSF, 7 mM β-mercaptoethanol, 0.1% Triton-X11, and Roche EDTA-free protease inhibitor cocktail). After the lysate was clarified by centrifugation, it was applied to a HisTrap column (GE Healthcare). The column was washed with buffer containing 50 mM HEPES, 1 M $NH_4Cl$, 10 mM $MgCl_2$, 7 mM β-mercaptoethanol, and 20 mM imidizole; RRF was eluted in the same buffer containing 400 mM imidazole. The protein was concentrated by ultrafiltration and applied to Sephacryl 16/60 size exclusion column (GE Healthcare). The RRF containing fractions were concentrated to 550 μM and stored at −80° C.

Preparation of Dye-Labeled Ribosome Complexes.

The labeling of L1 protein (Cy5-S55C) and $tRNA^{Phe}$ (Cy3-$s^4U8$) for smFRET experiment were performed as previously described (Munro 2010). 70S ribosomes were reconstituted with dye-labeled L1 and non-enzymatically initiated with mRNA and (Cy3-$s^4U8$) $tRNA^{Phe}$ by incubating with 1.5 molar excess of each over ribosomes at 37° C. for 10 minutes. The mRNA used has the same sequence as the one used in crystallization except for biotin modification at the 5' end to enable surface immobilization.

Single-Molecule Fluorescence Experiments.

All single-molecule fluorescence experiments were performed at room temperature in an MES-Polymix buffer that resembled the crystallization condition (50 mM MES, pH 6.5, 5.0 mM $MgCl_2$, 350 mM $NH_4Cl$, 5.0 mM putrescine, 5.0 mM spermidine, 5 mM β-mercaptoethanol and 0.5 mM EDTA). Oxygen scavenging and triplet-state quenching systems used were as previously described (Dave 2009). The smFRET data were acquired with the software sold under the trade name METAMORPH (Molecular Devices), and analyzed sold under the trade name MATLAB (Mathwork) and the software available under the trade name QUB, available at the website provided by the State University of New York at Buffalo as previously described (Munro, Altman et al. 2010). Subunit release was monitored by directly exciting the Cy5 fluorophore within surface-immobilized ribosome complexes with a 640 nm laser (Cube, Coherent) at 10 mW power. Time lapse imaging of the recycling reaction was performed by acquiring snapshot images (40 millisecond integration time) every 20 seconds over the course of 20 minutes. Changes in fluorescence intensity were analyzed and plotted using the computer program sold under the trade name ORIGIN (OriginLab).

Ribosome Recycling by smFRET

The dependence of subunit release on RRF, EF-G and GTP under crystallographic buffer conditions was monitored by the loss of Cy5-labeled L1 fluorescence in 50S subunits from surface-immobilized ribosome complexes carrying Cy3-labeled $tRNA^{Phe}$ in the P site. The results are shown in FIG. 3 where complexes imaged in the absence of factors (diamonds) or in the presence of 10 μM RRF (circles), 20 μM EF-G/2 mM GTP (inverted triangles), 10 μM RRF/20 μM EF-G/2 mM GDPNP (triangles) or 10 μM RRF/20 μM EF-G/2 mM GTP (squares). Data reflect the mean±SD of normalized Cy5 fluorescence intensity as a function of time from three experimental replicates.

Dynamics between the L1 stalk and P-site $tRNA^{Phe}$. As previously reported (Munro 2010), complexes bearing (Cy5-S55C) L1 protein and (Cy3-$s^4U8$) $tRNA^{Phe}$ achieve a high-FRET state upon the simultaneous occurrence of hybrid state formation (P/E) and L1 stalk closure. (A) Representative single-molecule fluorescence and FRET trajectories obtained from ribosome complexes bearing Cy3 labeled deacylated P-site $tRNA^{Phe}$ and Cy5 labeled L1 protein, imaged at 40 millisecond time resolution at room temperature in buffer conditions resembling those used in crystallographic experiments. Idealization of the smFRET trajectory, as previously described (Munro 2010), is overlaid. The boxed region in the upper panel shows an expanded region of the smFRET trajectory. (B) Individual FRET trajectories summed into population FRET histograms to reveal changes in relative population with increasing RRF concentrations. (C) RRF-induced stabilization of the unlocked state of the ribosome (hybrid P/E tRNA; closed L1 stalk), detected by the decrease in the transition rate out of a high-FRET state between Cy5-labeled protein L1 and Cy3-labeled P-site $tRNA^{Phe}$ (FIG. 3). The apparent $K_d$ for RRF based on the decrease in the transition rate is 5.7 μM.

Using FRET to Assess Conditions to Stabilize Ribosome in Hybrid Conformations.

Using smFRET with fluorophore-labeled tRNA and fluorophore labeled L1 protein, various parameters are explored to find conditions that stabilize the ribosome in a hybrid state. Various precipitants are added, mutant tRNAs are added, ion concentrations, particularly for Mg are varied, ionic strength is varied, antibiotics are included and pH is varied between 5.5 to 6.5.

Ribosome Purification and Crystallization.

Ribosomes lacking protein S1 were purified from E. coli strain MRE600 using sucrose gradient centrifugation, as described (Blaha 2000). Ribosomes were crystallized at 18° C. using microbatch 96-well plates and buffers containing 4.0-6.0% 2-methyl-2,4-pentanediol (MPD), 4.1-4.5% PEG 8000, 4.0 mM $MgCl_2$, 380 mM $NH_4Cl$, 5.7 mM putrescine, 5.0 mM spermidine, 10 mM Tris plus 40 mM MES, pH 6.5-7.0, and 0.25 mM EDTA. Ribosome complexes were formed by incubating 4 μM deacylated $tRNA^{Phe}$ and 8 μM mRNA of sequence 5'-GGCAAG GAGGUAAAAUUCUA-CAAA-3' (SEQ ID NO: 1; Dharmacon) with 2 μM ribosomes at 37° C. for 15 minutes. 8 μM RRF was then added and the samples were incubated for an additional 15 minutes at 37° C. Prior to crystallization, samples were subjected to ultrafiltration to remove excess ligands.

Data Collection and Processing.

Ribosome crystals were stabilized with crystallization buffer containing 7.0% MPD, 7.0% PEG 8000 and 24% PEG 400, pH 4.8, to allow cryocooling of the crystals to liquid nitrogen temperatures. Diffraction data were measured from crystals cooled to 100° K using 0.1-0.3° oscillations at beamlines 24ID-C at the Advanced Photon Source or at the Advanced Light Source (SIBYLS and 8.3.1 beamlines), each of which is equipped with an ADSC Q315 area detector. Data were reduced using XDS (Kabsch 1993), yielding the statistics shown in Table 1. The structures are deposited under PDB codes: fully rotated state: 3R8N, 3R8S; unrotated state: 3R8O, 3R8T (the letter O, not zero) and are incorporated herein by reference. The PDB coordinates are maintained by and searchable on several databases available on the web, for example, at the website of the Research Collaboratory for Structural Bioinformatics and the website of the Worldwide Protein Data Bank (wwPDB).

The structures of the intact E. coli 70S ribosome was determined at a resolution of ~3.2 Å (Table 1 and 2), based on crystals that contain two independent copies of the ribosome per asymmetric unit in a "top-top" polysome configuration (Brandt 2009). The validation statistics are provided in Table 3.

TABLE 1

X-ray crystallographic statistics

| | |
|---|---|
| Space group | $P2_12_12_1$ |
| unit cell (a, b, c in Å) | 211.67, 438.07, 613.42 |

TABLE 1-continued

X-ray crystallographic statistics

| Resolution (Å) | 70-3.0 |
|---|---|
| (high-resolution shell)* | (3.35-3.16) |
| $R_{merge}$† | 19.4 (57.7) |
| I/σ (I) | 7.4 (1.8) |
| Completeness (%) | 83.5 (66.1) |
| Measurement redundancy | 5.3 (3.3) |
| Unique reflections | 938,380 (101,586) |
| No. crystals used | 10 |

*Data beyond the high-resolution shell in parenthesis was used for refinement and map calculation, and extend to an I/σ (I) of about 1. Data are 92.5% complete in the 3.9 Å-3.6 Å resolution shell, and 99% complete in lower-resolution shells.
†All statistics not in parentheses include data over the whole reported resolution range.

TABLE 2

X-ray structure refinement

| Resolution (Å) | 40-3.0 | |
|---|---|---|
| No. Reflections | 938,304 | |
| $R_{free}$ Set | 19,021 | |
| R/$R_{free}$ (%)* | 20.2/26.1 | |
| No. non-H Atoms | 293,365 | |
| R.m.s. deviations | Bond lengths (Å) | 0.013 |
| | Bond angles (°) | 1.39 |
| Mean ADP values (Å²)† | State $R_0$ 70S | 29.0 |
| | State $R_F$ 70S | 24.6 |

*Refinement in Phenix (Adams 2010) with riding H atoms.
†Atomic displacement parameter values are reported as isotropic B-factors. B-factor model is 2 per residue, wxu weight set to 1.66.

TABLE 3

Validation statistics**

| | State $R_0$ 70S | | State $R_F$ 70S | |
|---|---|---|---|---|
| All-atom clashscore | 44.1 | 56th percentile | 38.5 | 68th percentile |
| Ramachandran outliers | 9.2% | 10th percentile | 8.4% | 12th percentile |
| Ribose pucker outliers | 1.6% | 73rd percentile | 1.9% | 70th percentile |
| Bond + angle outliers | 0.63% | | 1.77% | |

**From MolProbity (Chen 2010).
**From MolProbity (Chen 2010).

REFERENCES

Adams, P. D., P. V. Afonine, et al. (2010). "PHENIX: a comprehensive Python-based system for macromolecular structure solution." Acta Crystallogr D Biol Crystallogr 66(Pt 2): 213-21.

Agrawal, R. K., M. R. Sharma, et al. (2004). "Visualization of ribosome-recycling factor on the Escherichia coli 70S ribosome: functional implications." Proc Natl Acad Sci USA 101(24): 8900-5.

Ben-Shem, A., L. Jenner, et al. (2010). "Crystal structure of the eukaryotic ribosome." Science 330(6008): 1203-9.

Blaha, G., U. Stelzl, et al. (2000). "Preparation of functional ribosomal complexes and effect of buffer conditions on tRNA positions observed by cryoelectron microscopy." Methods Enzymol 317: 292-309.

Blanchard, S. C., H. D. Kim, et al. (2004). "tRNA dynamics on the ribosome during translation." Proc Natl Acad Sci USA 101(35): 12893-8.

Brandt, F., S. A. Etchells, et al. (2009). "The native 3D organization of bacterial polysomes." Cell 136(2): 261-71.

Cayama, E., A. Yepez, et al. (2000). "New chromatographic and biochemical strategies for quick preparative isolation of tRNA." Nucleic Acids Res 28(12): E64.

Chen, V. B., W. B. Arendall, 3rd, et al. (2010). "MolProbity: all-atom structure validation for macromolecular crystallography." Acta Crystallogr D Biol Crystallogr 66(Pt 1): 12-21.

Dunkle, J. A. and J. H. Cate (2010). "Ribosome structure and dynamics during translocation and termination." Annu Rev Biophys 39: 227-44.

Fischer, N., A. L. Konevega, et al. (2010). "Ribosome dynamics and tRNA movement by time-resolved electron cryo-microscopy." Nature 466(7304): 329-33.

Frank, J. and R. K. Agrawal (2000). "A ratchet-like inter-subunit reorganization of the ribosome during translocation." Nature 406(6793): 318-22.

Gao, N., A. V. Zavialov, et al. (2005). "Mechanism for the disassembly of the posttermination complex inferred from cryo-EM studies." Mol Cell 18(6): 663-74.

Junemann, R., J. Wadzack, et al. (1996). "In vivo deuteration of transfer RNAs: overexpression and large-scale purification of deuterated specific tRNAs." Nucleic Acids Res 24(5): 907-13.

Kabsch, W. (1993). "Automatic processing of rotation diffraction data from crystals of initially unknown symmetry and cell constants." J. Appl. Cryst. 26: 795-800.

Lancaster, L., M. C. Kiel, et al. (2002). "Orientation of ribosome recycling factor in the ribosome from directed hydroxyl radical probing." Cell 111(1): 129-40.

Moazed, D. and H. F. Noller (1989). "Intermediate states in the movement of transfer RNA in the ribosome." Nature 342(6246): 142-8.

Munro, J. B., K. Y. Sanbonmatsu, et al. (2009). "Navigating the ribosome's metastable energy landscape." Trends Biochem Sci 34(8): 390-400.

Munro, J. B., R. B. Altman, et al. (2010). "A fast dynamic mode of the EF-G-bound ribosome." EMBO J 29(4): 770-81.

Munro, J. B., R. B. Altman, et al. (2010). "Spontaneous formation of the unlocked state of the ribosome is a multistep process." Proc Natl Acad Sci USA 107(2): 709-14.

Ratje, A. H., J. Loerke, et al. (2010). "Head swivel on the ribosome facilitates translocation by means of intra-subunit tRNA hybrid sites." Nature 468(7324): 713-6.

Savelsbergh, A., M. V. Rodnina, et al. (2009). "Distinct functions of elongation factor G in ribosome recycling and translocation." RNA 15(5): 772-80.

Schmeing, T. M. and V. Ramakrishnan (2009). "What recent ribosome structures have revealed about the mechanism of translation." Nature 461(7268): 1234-42.

Semenkov, Y. P., M. V. Rodnina, et al. (2000). "Energetic contribution of tRNA hybrid state formation to translocation catalysis on the ribosome." Nat Struct Biol 7(11): 1027-31.

Sternberg, S. H., J. Fei, et al. (2009). "Translation factors direct intrinsic ribosome dynamics during translation termination and ribosome recycling." Nat Struct Mol Biol 16(8): 861-8.

von Ehrenstein, G. and K. M. Lawrence Grossman (1967). Isolation of sRNA from intact Escherichia coli cells. Methods in Enzymology, Academic Press. Volume 12, Part 1: 588-596.

Zavialov, A. V. and M. Ehrenberg (2003). "Peptidyl-tRNA Regulates the GTPase Activity of Translation Factors." Cell 114(1): 113-22.

Zhang, W., J. A. Dunkle, et al. (2009). "Structures of the ribosome in intermediate states of ratcheting." Science 325 (5943): 1014-7.

We claim:

1. A method for selecting a crystallization for a biomolecule comprising:
   (a) labeling the biomolecule with a donor and acceptor fluorophore sufficiently spaced to report time-dependent dynamics of multiple conformations of the biomolecule by single molecule fluorescence resonance energy transfer (smFRET), wherein said multiple conformations includes a first conformation;
   (b) placing the labeled biomolecule under different crystallization conditions;
   (c) detecting fluorescence resonance energy transfer between the donor and acceptor fluorophores for each condition over a period of time;
   (d) determining the amount of time the biomolecule spends in said first conformation, relative to other conformation or conformations; and
   (e) selecting the crystallization condition under which the biomolecule spends more time in said first conformation relative to other conformation or conformations.

2. The method of claim 1, wherein different crystallization conditions comprises different buffers, pH, temperature, salts, chelators, precipitants, or one or more ligands.

3. The method of claim 1, wherein more than one crystallization condition is selected.

4. The method of claim 1, wherein said biomolecule comprises multiple subunits.

5. The method of claim 4, wherein said fluorophores are on the same subunit or different subunits of said biomolecule.

6. The method of claim 1, wherein said biomolecule is protein, a peptide, a proteoliposome, a nucleic acid, or a complex of any combination thereof.

7. The method of claim 6 wherein said complex is an RNA protein complex selected from the group consisting of a ribosome, a spliceosome, a telomerase or a microRNA complex.

8. The method of claim 6 wherein said nucleic acid is a riboswitch or a ribozyme.

9. The method of claim 6 wherein said protein is a membrane protein.

10. The method of claim 9, wherein said membrane protein is a viral envelope protein, an ion channel, an excitatory amino acid transporter (EAAT) transporter protein, a major facilitator superfamily (MFS) transporter protein, an ATP-binding cassette (ABC) transporter or a P-type ATPase.

11. The method of claim 6, wherein said biomolecule is selected from the group consisting of a G-protein-coupled receptor (GPCR), a neurotransmitter:sodium symporter (NSS) protein, a protein kinase, an aminoacyl-tRNA synthetase, a caspase, or a motility or motor protein.

12. The method of claim 1, wherein said biomolecule is directly or indirectly surface immobilized for smFRET detection.

13. The method of claim 1, wherein said biomolecule is imaged using fluorescence correlation spectroscopy.

14. The method of claim 11, wherein the motility or motor protein is kinesin or myosin.

15. The method of claim 1, wherein said first conformation is associated with a high-FRET signal.

* * * * *

SEQUENCE LISTING

```
<160> NUMBER OF SEQ ID NOS: 1

<210> SEQ ID NO 1
<211> LENGTH: 24
<212> TYPE: RNA
<213> ORGANISM: Artificial Sequence
<220> FEATURE:
<223> OTHER INFORMATION: synthetic ribosomal mRNA initiator

<400> SEQUENCE: 1
ggcaaggagg uaaaauucua caaa                                              24
```